United States Patent [19]

Hasegawa et al.

[11] Patent Number: 5,160,740
[45] Date of Patent: Nov. 3, 1992

[54] MACROMOLECULAR ENDOPLASMIC RETICULUM

[75] Inventors: Etsuo Hasegawa, Ohmiya; Shinji Takeoka, Tokyo; Hiroyuki Ohno, Tokyo; Hiroyuki Nishide, Tokyo; Eishun Tsuchida, Tokyo, all of Japan

[73] Assignee: Nippon Oil & Fats Co., Ltd., Tokyo, Japan

[21] Appl. No.: 515,955

[22] Filed: Apr. 27, 1990

[30] Foreign Application Priority Data

Apr. 27, 1989 [JP] Japan .................................. 1-110682
Feb. 14, 1990 [JP] Japan .................................. 2-33256

[51] Int. Cl.⁵ .............................................. A61K 9/127
[52] U.S. Cl. ...................................... 424/450; 526/277
[58] Field of Search ............... 424/450; 428/402.2; 264/4.1, 4.3, 4.6; 436/829; 260/403

[56] References Cited

U.S. PATENT DOCUMENTS

| | | | |
|---|---|---|---|
| 4,348,329 | 9/1982 | Chapman | 260/403 |
| 4,485,045 | 11/1984 | Regen | 260/403 |
| 4,560,599 | 12/1985 | Regen | 260/403 X |
| 4,564,475 | 1/1986 | Masaichiro | 260/403 X |
| 4,861,521 | 8/1989 | Suzuki et al. | 260/403 |
| 4,877,501 | 10/1989 | Schnur et al. | 260/403 X |
| 4,933,114 | 6/1990 | O'Brien et al. | 260/403 |
| 4,990,291 | 2/1991 | Schoen et al. | 424/450 X |
| 5,004,566 | 4/1991 | Schnur et al. | 260/403 |
| 5,061,484 | 10/1991 | Heldebrant | 514/672 X |

OTHER PUBLICATIONS

Freeman et al. "Polymerizable Liposomes" from Liposomes As Drug Carriers, ed. Gregoridas, pp. 821-839 (1988).
Hupfer et al. Makromol. Chem. 182 247-253 (1981).
Agnew. Chem. Int. Ed. Engl. 20 305-325 (1981); pertinent pp. 314-317.
Dorn et al, J. Amer. Chem. Soc. (1984) 106, 1627-1633.

Primary Examiner—Thurman K. Page
Attorney, Agent, or Firm—Browdy and Neimark

[57] ABSTRACT

The present invention relates to a micromolecular endoplasmic reticulum which comprises a polymer obtained by polymerization of a mixture containing one or more polymerizable phospholipids, cholesterol and one or more polymerizable fatty acid. The macromolecular endoplasmic reticulum in which surface charge is fixed to negative can be used as a carrier of medicine, enzyme, hemoglobin, etc. in industrial fields or medical fields.

8 Claims, No Drawings

MACROMOLECULAR ENDOPLASMIC RETICULUM

BACKGROUND OF THE INVENTION

The present invention relates to a macromolecular endoplasmic reticulum in which surface charge is fixed to negative.

It is possible to utilize the macromolecular endoplasmic reticulum of the present invention as a carrier of medicine, enzyme, hemoglobin, etc. in industrial fields or medical fields There are many reports for trying to enhance the effectivity of useful materials such as medicine and enzyme by capsulizing in fine capsules. In the initial trials, synthetic macromolecular compounds such as polystyrene and nylon were used as membrane materials.

However, since these materials were toxic and they caused thrombus because they had large grain size, they were unusable.

Recently, it is noted to use a fine microcapsule (endoplasmic reticulum) made of natural phospholipid as membrane materials having little toxicity, particularly, as a carrier of medicine. The grain size of the micro-capsule can be optionally adjusted to 0.02 μm to a few μm. Then the problems such as thrombosis are evitable by determination of proper grain size. However, there are problems that the endoplasmic reticulum has neither shelf stability nor retention in blood because it is physically and chemically unstable in vivo and it tends to decompose easily.

The other hand, hemoglobin carrying oxygen in the body of mammals is utilized as an agent for carrying, storing or absorbing oxygen. Particularly, it is often used as materials of a oxygen carrying liquid. In the body, hemoglobin is contained in red blood corpuscles. Imitating this, a oxygen-carrier containing a hemoglobin aqueous solution in a endoplasmic reticulum which consists of a bilayer membrane was reported (Arbing Frank Miller et al., Japanese patent publication No. 60-26092; C. Anthony Hunt, Japanese patent publication No. 58-183625; Suzuki et al., Japanese patent publication No. 62-178521). All of the endoplasmic reticula which contain hemoglobin are utilized as membrane materials using natural or synthetic non-polymerizable lipid or a lipid mixture. On such endoplasmic reticula, as described above, it is broadly examined to use not only as a carrier of a hemoglobin aqueous solution but also as that of medical supplies. Since these endoplasmic reticula are prepared from natural compounds, the safety is appreciated. However, these endoplasmic reticula can not be preserved for a long time, and they are physically and chemically unstable and easily decomposed. Particularly, the problem is that they can not be kept in blood. For this reason, it is earnestly studied to stabilize the endoplasmic reticula.

For example, as a method for stabilizing an endoplasmic reticulum, a method for polymerizing a lipid bimolecular membrane by using polymerizable phospholipids (there are many derivatives of a phosphatidylcholine type) is reported (H. Ringsdorf et al., Angewandte Chemie International Edition English, vol. 20, page 305 (1981), and others). In this method, it is tried to give physical stability to the membrane by polymerization. There is a report in which, after enclosing a hemoglobin aqueous solution in an endoplasmic reticulum obtained from one of these polymerizable phospholipids (a phosphatidylcholine derivative having diyne radicals as polymerizable residue groups) and cholesterol, the reticulum is polymerized to obtain a macromolecular endoplasmic reticulum containing hemoglobin (J. A. Hayward et al., PCT WO 85/04326).

However, for stabilizing microcapsules in a living body, especially, in blood, it is necessary to devise to maintain proper zeta potential of liposomes and keep the surface charge negative, for reducing the interaction between microcapsules and biological cells and components to a minimum. For devising it, in cases of common (non-polymerized) endoplasmic reticula and the above macromolecular endoplasmic reticulum, non-polymerized lipids having negative electric charge, for example, non-polymerizable fatty acids, phosphatidic acid, dicetyl phosphoric acid, phosphatidyl serine have been used. However, in blood, these components are easily extracted from membranes by a component in a living body such as high density lipoprotein (HDL), so that the stability of these microcapsules was insufficient.

SUMMARY OF THE INVENTION

The object of the present invention is to provide a stable macromolecular endoplasmic reticulum having negative charge on the surface of capsule membranes, especially, a macromolecular endoplasmic reticulum in which negative charge components participating in polymerization are fixed by covalent bonds on the membranes.

Namely, the present invention resides in a macromolecular endoplasmic reticulum which comprises a polymer obtained by polymerization of a mixture containing one or more polymerizable phospholipids, cholesterol and one or more polymerizable fatty acids.

As the polymerizable phospholipids, phospholipids having polymerizable radicals in addition to conventional phosphatidylcholine used in general may be used. When a negative polymerizable phospholipid is used, it is unnecessary to participate in polymerization with the polymerizable fatty acids as constituents having negative change. Accordingly, the present invention is important in the use of phospholipids (in general, phosphatidylcholine derivatives) having neutral charge and polymerizable radicals.

As the polymerizable fatty acids, any compound having polymerizability can be used. Fatty acids having 12 or more carbons are preferable.

Considering efficiency of capsulation of hemoglobin, the mole ratio of the polymerizable phospholipid / the polymerizable fatty acid is preferably from 6:1 to 2:1, more preferably from 5:1 to 3:1. The mole ratio of the polymerizable phospholipid / cholesterol is preferably from 1:2 to 3:2, more preferably from 3:4 to 4:3. Further, considering the efficiency of capsulation of hemoglobin, the combination of the polymerizable phospholipid and the polymerizable fatty acid with cholesterol is advisably selected.

The combination of the polymerizable phospholipid represented by the following formula (I) or (II) and the polymerizable fatty acid represented by the following formula (III) is exemplified.

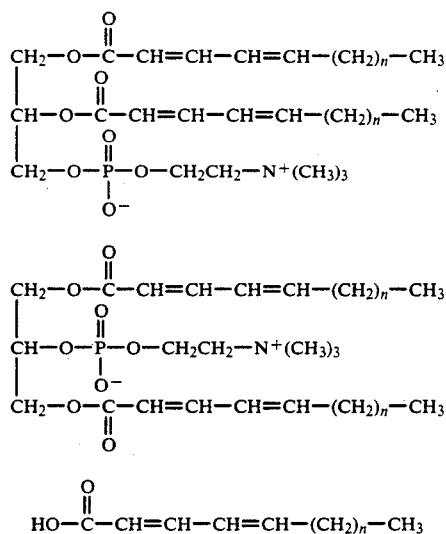

wherein n is an integer of 12, 10, 8 or 6. As seen in the above formulas, the polymerizable double bonds are concentrated at the polar end of the fatty acids and the fatty acid component of the phospholipid.

DETAILED DESCRIPTION OF THE INVENTION

The production of the endoplasmic reticulum comprising a mixture of a polymerizable phospholipid, a polymerizable fatty acid and cholesterol can be performed by a conventional method (G. Gregoriades. "Liposome Technology"vol. 1, C. R. C. Press (1983), etc.). As an example, to the powder obtained by freeze-drying a mixture of a polymerizable phospholipid, a polymerizable fatty acid and cholesterol in benzene, water, buffer, isotonic physiological saline (pH 5 to 9, preferably 6 to 8) or the like are added. The mixture is treated by ultrasonic waves (an ultrasonic oscillator of a probe type or a bath type) at a temperature of below zero to 60° C. under an inert (nitrogen, argon, carbon monoxide, etc.) atmosphere to obtain an endoplasmic reticulum dispersion. The other hand, to said powder mixture, water, buffer and isotonic physiological saline are added and the mixture can be treated with a Voltex mixer at a temperature of 5° to 37° C. for 5 to 60 minutes to obtain a multi-layer endoplasmic reticulum (particle size: ~10 μm). All sorts of medicine, enzyme, protein and the like can be enclosed in the endoplasmic reticulum.

As an example, it is possible to enclose hemoglobin in the endoplasmic reticulum by the following method. As well known, hemoglobin solution may have an adequate amount of a reductant such as nicotinamide adenine dinucleotide (reduced form), ascorbic acid etc. for preventing the increase of methemoglobin content and of an oxygen-binding affinity regulator for hemoglobin such as 2,3-diphosphoglycerate, inositol hexaphosphate etc. for adjusting the oxygen affinity of the encapsulated hemoglobin. A concentrated hemoglobin aqueous solution (having a hemoglobin concentration of 10 to 50 wt %, preferably 15 to 35 wt %) is added to said lipid mixture and treated with a Voltex mixer at a temperature of 5 to 37° C. under an inert atmosphere (nitrogen gas, argon gas or carbon monoxide gas) for 5 to 60 minutes to obtain a solution of a multi-layer endoplasmic reticulum (particle size: ~10 μm) in which hemoglobin is enclosed. After passing the solution of the multi-layer endoplasmic reticulum enclosing hemoglobin through, for example, porous polycarbonate membranes (hole size: 8, 5, 3, 2, 1, 0.6, 0.4 μm or the like), the solution is purified by a gel permeation chlomatograph on a suitable ultrafiltration column (for example, Sepharose CL-4B manufactured by Pharmacia Fine Chemical Company) or an ultrafiltration membrane (for example, AC-1760 type hollow fiber manufactured by Asahi Medical Company in Japan) (isotonic physiological saline (pH 7.4) is used as a medium, while hemoglobin which is not enclosed in the multi-layer endoplasmic reticulum is removed, at the same time, the hemoglobin endoplasmic reticulum solution is concentrated, and the desired endoplasmic reticulum (particle size: 0.1 to 0.6 μm) dispersion is obtained.

Further, isotonic physiological saline is added to said freeze-dried lipid mixture, the solution obtained is treated by ultrasonic waves at a temperature of zero to 60° C. under an inert atmosphere (nitrogen, argon etc.), and a dispersion containing a single-layer endoplasmic reticulum (particle size: 20 to 60 nm) is prepared. After adding a concentrated hemoglobin solution to the dispersion, the solution is treated by freezing and thawing ($-78°$ C. to room temperature) to obtain a solution enclosing the hemoglobin aqueous solution in the endoplasmic reticulum. After passing the solution obtained through porous poly-carbonate membranes (hole size: 8, 5, 3, 2, 1, 0.6, 0.4 μm or the like), the solution is washed with a suitable ultrafiltration membrane (for example, AC-1760 type hollow fiber manufactured by Asahi Medical Company in Japan) (isotonic physiological saline (pH 7.4) is used as a medium), hemoglobin which is not enclosed in the endoplasmic reticulum is removed, at the same time, the hemoglobin endoplasmic reticulum solution is concentrated, and the objective hemoglobin endoplasmic reticulum solution (particle size: 0.1 to 0.6 μm) dispersion is obtained.

For preparing macromolecular endoplasmic reticulum by polymerization of the endoplasmic reticulum, the polymerization can be performed by irradiation of ultraviolet rays or gamma rays under an inert atmosphere (nitrogen gas, argon gas or carbon monoxide gas), or by addition of a suitable initiator. When materials (medicine, enzyme, protein or the like) containing in the endoplasmic reticulum are unstable to heat, a low-temperature initiator is efficiently used. As an example, a polymer can be obtained by irradiation of visible rays at a low temperature ($\sim 10°$ C.) in the presence of azo-bis(2-amidino-propane) dihydrochloride. Further, a polymer can be obtained by using a $NHSO_3 / K_2S_2O_8$ redox initiator at a low temperature. Any polymerization method can be used without limits within the region of the present invention. The progress of the polymerization can be confirmed by strength decrease of a property absorption band (for example at 255 nm for the compounds (I), (II) and (III) of ultraviolet spectra. After polymerizing the endoplasmic reticulum, the obtained polymer solution as it is, or after adding a proper radical scavenger (cysteine (hydrochloride), mercaptoethanol, dithiothreitol or the like), is purified with a proper ultrafiltration column (for example, Sepharose CL-4B manufactured by Pharmacia Fine Chemical Company) or an ultrafiltration membrane (for example, AC-1760 type hollow fibers manufactured by Asahi Medical Company), then the solution purified is concentrated, and a macromolecular endoplasmic reticulum dispersion or a dispersion of the macromolecular endoplasmic reticulum which encloses hemoglobin can be obtained.

Merits of the invention are as follows.

Since the macromolecular endoplasmic reticulums obtained in the present invention are prepared by the polymerization of a polymerizable fatty acid and a polymerizable neutral phospholipid with or without cholesterol, the microcapsules are stable mechanically and expected to show reduced interaction with biological cells or components owing to their controlled zeta potentials based on the negative charge of the fatty acid, which is covalently bound to the polymerized bilayer membrane. The efficiency for enclosing materials (hemoglobin etc.) into them is also enhanced by the presence of a polymerizable fatty acid as a membrane component.

DETAILED DESCRIPTION OF PREFERRED EMBODIMENTS

The following examples illustrate the present invention more specifically, but these will not always be precise in practical application.

EXAMPLE 1

2.05 g (2.6 mmol) of 1,2-bis(octadeca-trans, 2-trans, 4-dienoyl)-Sn-glycero-3-phosphocholine (a compound of n=12 in the formula (I)), 0.15 g (0.5 mmol) of octadecatrans, 2-trans, 4-dienoic acid (a compound of n=12 in the formula (III)) and 0.81 g (2.1 mmol) of cholesterol were dissolved in 40 ml of benzene and the solution obtained was freeze-dried. To the powder obtained, 60 ml of 5 mM Tris buffer (pH 7.4, containing 0.9 wt % sodium chloride) was added, and the mixture was treated by ultrasonic waves (60 W, 15 minutes) with cooling under a nitrogen atmosphere. The single-layer endoplasmic reticulum aqueon dispersion obtained was charged in a quarz glass vessel. After the atmosphere was replaced with nitrogen, the vessel was sealed. To the dispersion, 3.1 ml of a 50 mM azobis(2-diaminopropane)dihydrochloride aqueous solution as an initiator of photosensitized polymerization was added and cooled to 8° C. Visible lights in which short wave lights of less than 360 nm were cut with a filter were irradiated to the mixture with a high-pressure mercury lamp (UVL-100 manufactured by Riko Kagaku Sangyo in Japan) to decompose the initiator, and the polymerizable fatty acid was polymerized. After twelve hours, the rate of polymerization was 50% (it was determined by the variation with time of absorbance of a 255 nm absorption band due to diene radicals using a Shimadzu UV-2000 spectrophotometer). The polymer solution was treated with a gel permeation chromatography on Sepharose CL-4B, (medium:5 mM Tris buffer (pH 7.4, containing 0.9 wt % sodium chloride)) to remove low-molecular weight compounds and the desired aqueous dispersion containing a macromolecular endoplasmic reticulum was obtained. The particle size of the reticulum determined by light scattering measurement using a Coulter N4D (Coulter Electronics Co.) was about 30 nm. The stability of the macromolecular endoplasmic reticulum was compared with the nonpolymerized endoplasmic reticulum by addition of a surface-active agent (Triton X-100). The nonpolymerized endoplasmic reticulum was thoroughly destroyed by adding the surface-active agent (Triton X-100) of 3 mM, while the macromolecular endoplasmic reticulum was not destroyed by adding the surface active agent (Triton X-100) of 12 mM and remained stable.

EXAMPLE 2

0.782 g (1.0 mmol) of 1,2-bis(octadeca-trans, 2-trans, 4-dienoyl)-Sn-glycero-3-phosphocholine (a compound of n=12 in the formula (I)), 0.080 g (0.28 mmol) of octadeca-trans, 2-trans, 4-dienoic acid (a compound of n=12 in the formula (III)) and 0.386 g (1.0 mmol) of cholesterol were dissolved in 30 ml of benzene and the solution obtained was freeze-dried. To the powder obtained, 20 ml of 5 mM Tris buffer (pH 7.4, containing 0.9 wt % sodium chloride) was added, and the mixture was treated with a Voltex mixer at a room temperature (20°-25° C.) for 10 minutes under a nitrogen atmosphere to obtain a solution of a multi-layer endoplasmic reticulum. Then, the solution was passed through porous polycarbonate membranes (hole size : 1.0, 0.6, 0.4, 0.2 μm) with an extruder (Lipex Biomembranes Inc.) to obtain an aqueous dispersion containing the endoplasmic reticulum having a particle size of 180 nm. 10 ml of the dispersion was charged in a glass vessel. After the atmosphere was replaced with nitrogen, the vessel was sealed. After cooling the vessel at 5° C., 0.07 ml of 5 wt % sodium hydrogen sulfite aqueous solution and 0.17 ml of 5 wt % potassium persulfate were added. The mixture was reacted for 6 hours (rate of polymerization:43%) to obtain an aqueous dispersion containing a macromolecular endoplasmic reticulum. The dispersion was treated with a gel permeation chromatograph on Sepharose CL-4B (medium:5 mM Tris buffer (pH7.4, containing 0.9 wt % sodium chloride)) to remove low-molecular weight compounds and the desired aqueous dispersion containing the macromolecular endoplasmic reticulum (particle size:180 nm) was obtained.

EXAMPLE 3

1.173 g (1.50 mmol) of 1,3-bis(octadeca-trans, 2-trans, 4-dienoyl)-rac-glycero-2-phosphocholine (a compound of n=12 in the formula (II)), 0.180 g (0.64 mmol) of octadeca-trans, 2-trans, 4-dienoic acid (a compound of n=12 in the formula (III)) and 0.579 g (1.50 mmol) of cholesterol were treated by the same procedure as in Example 1 to obtain a macromolecular endoplasmic reticulum (particle size:35 nm).

EXAMPLE 4

2.346 g (3.0 mmol) of 1,2-bis(octadeca-trans, 2-trans, 4-dienoyl)-Sn-glycero-3-phosphocholine (a compound of n=12 in the formula (I)), 0.240 g (0.85 mmol) of octadeca-trans, 2-trans, 4-dienoic acid (a compound of n=12 in the formula (III)) and 1.158 g (3.0 mmol) of cholesterol were dissolved in 40 ml of benzene and the solution obtained was freeze-dried. To the powder obtained, 25 ml of 5 mM Tris buffer (pH 7.4, containing 0.9 wt % sodium chloride) was added, and the mixture was treated by ultrasonic waves (60 W, 20 minutes) with water cooling under a nitrogen atmosphere. A single-layer endoplasmic reticulum aqueous dispersion was obtained. To 20 ml of the solution, 40 ml of a 35 wt % human hemoglobin aqueous solution was added, and frozen (−78° C.) and then melted (at room temperature) twice. The solution was passed through porous polycarbonate membranes (hole size: 8, 5, 3, 2, 1, 0.6 μm and the like). The solution was treated with a gel permeation chromatograph on Sepharose CL-4B (medium:5 mM Tris buffer (pH 7.4, containing 0.9 wt % sodium chloride)) to remove non-enclosed hemoglobin under a nitrogen gas atmosphere and a hemoglobin endoplasmic reticulum (particle size:0.5 μm) was obtained. 10 ml of the solution containing the endoplasmic reticulum was charged in a quartz glass vessel. After the atmosphere was replaced with nitrogen, the vessel was sealed and cooled to 8° C. To the solution, 0.3 ml of 50 mM azobis(2-diaminopropane)dihydrochloride aqueous solution as an initiator of photosensitized polymerization was added. Visible lights in which short wave lights of less than 360 nm were cut with a filter were irradiated to the solution with a high-pressure mercury lamp (UVL-100 manufactured by Riko Kagaku Sangyo in Japan) to polymerize the polymerizable lipids. After 10 hours, the rate of polymerization was 26% (it was determined by the variation with time of absorbance at 255 nm). The polymer solution was treated with a gel permeation chromatograph on Sepharose CL-4B, medium:5 mM Tris buffer (pH 7.4, containing 0.9 wt % sodium chloride) to remove low-molecular weight compounds and the desired aqueous dispersion containing the macromolecular endoplasmic reticulum (particle size:0.5 μm) was obtained. The efficiency for enclosing hemoglobin (the ratio of the amount of hemoglobin enclosing in the endoplasmic reticulum / the amount of raw hemoglobin (%)) was 15%. The denaturation of hemoglobin was not observed, which was judged from the visible absorption spectrum. The stability of the macromolecular endoplasmic reticulum was compared with the nonpolymerized endoplasmic reticulum by addition of a surface-active agent (Triton X-100). The nonpolymerized endoplasmic reticulum was thoroughly destroyed by adding the surface-active agent (Triton X-100) of 3 mM, while the macromolecular endoplasmic reticulum was not destroyed by adding the surface active agent (Triton X-100) of 10 mM and remained stable. The leakage of hemoglobin was less than 2% after storing at 4° C. and 37° C. for 6 days.

EXAMPLE 5

1.845 g (2.36 mmol) of 1,2-bis(octadeca-trans, 2-trans, 4-dienoyl)-Sn-glycero-3-phosphocholine (a compound of n=12 in the formula (I)), 0.135 g (0.48 mmol) of octadeca-trans, 2-trans, 4-dienoic acid (a compound of n=12 in the formula (III)) and 0.729 g (1.89 mmol) of cholesterol were dissolved in 30 ml of benzene and the solution obtained was freeze-dried. To the powder obtained, 50 ml of a 35% human hemoglobin aqueous solution was added, and the mixture was treated with a Voltex mixer at a room temperature (20°-25° C.) for 10 minutes under a nitrogen atmosphere to obtain a solution of multi-layer endoplasmic reticulum. Then, the solution was passed through a porous polycarbonate membrane (hole size: 8, 5, 3, 2, 1, 0.6, etc. μm) to remove nonenclosed hemoglobin and an aqueous dispersion containing an endoplasmic reticulum was obtained. 20 ml of the dispersion was charged in a glass vessel. After the atmosphere was replaced with nitrogen, the vessel was sealed. After cooling the vessel at 5° C., 0.05 ml of an aqueous solution of 5 wt % sodium hydrogen sulfite and 0.12 ml of an aqueous solution of 5 wt % potassium persulfate were added. The mixture was reacted for 4 hours (yield of polymerization: 30%) to obtain an aqueous dispersion containing a macromolecular endoplasmic reticulum. The dispersion was treated with a gel filter column (filler:Sephalose CL-4B, medium:5 mM Tris buffer (pH7.4, containing 0.9 wt % sodium chloride)) to remove low-molecular weight compounds and the desired aqueous dispersion containing the macromolecular endoplasmic reticulum (particle size:0.4 μm) was obtained. The efficiency for enclosing hemoglobin (the ratio of the amount of hemoglobin enclosing in the endoplasmic reticulum / the amount of raw hemoglobin (%)) was 29%. The denaturation of hemoglobin was not observed by measuring a visible absorption spectrum. The stability of the macromolecular endoplasmic reticulum was compared with the nonpolymerized endoplasmic reticulum by addition of a surface-active agent (Triton X-100). The nonpolymerized endoplasmic reticulum was thoroughly destroyed by adding the surface-active agent (Triton X-100) of 3 mM, while the macromolecular endoplasmic reticulum was not destroyed by adding the surface active agent (Triton X-100) of 10 mM and remained stable. The leakage of hemoglobin was less than 2% after storing the macromolecular endoplasmic reticulum at 4° C. and 37° C. for 6 days.

EXAMPLE 6

1.880 g (2.40 mmol) of 1,3-bis(octadeca-trans, 2-trans, 4-dienoyl)-rac-glycero-2-phosphocholine (a compound of n=12 in the formula (II)), 0.192 g (0.69 mmol) of octadeca-trans, 2-trans, 4-dienoic acid (a compound of n=12 in the formula (III)) and 0.794 g (2.06 mmol) of cholesterol were treated by the same procedure as in Example 5 to obtain a macromolecular endoplasmic reticulum (particle size:0.6 μm). The efficiency for enclosing hemoglobin was 20%.

EXAMPLE 7

In a 10 ml Erlenmeyer flask, 300 mg of a lipid mixture (1,2-bis octadeca-trans, 2-trans, 4-dienoyl)glycero-3-phosphocholine / cholesterol / octadeca-2,4-dienoic acid, mole ratio 7:7:2) obtained by freeze-drying in benzene, 6 ml of a purified hemoglobin aqueous solution (17 g/dl, methemoglobin content was 2.6%, carbon monoxide was blown for 3 minutes (the production of a carbon monoxide complex was confirmed by a characteristic absorption band ($\lambda_{max}$:419, 439 and 569 nm) of a visible absorption spectrum)) obtained by dissolving equimolecular amounts of hemoglobin and inositol hexaphosphate and 5 mM NADH, and a small amount of glass beads were charged and hydrated for 15 minutes at 4° C. Then, the hydrate was treated with a Voltex mixer for 15 minutes. The solution was treated with polycarbonate membranes (extruders) having hole diameters of 8, 5, 3, 2, 1, 0.6 and 0.4 m in order. A fraction of an endoplasmic reticulum enclosing hemoglobin and a fraction of free hemoglobin were separated from 5 ml of a sample passed through the 0.4 μm membrane with a Sepharose CL-4B column (manufactured by Pharmacia Chemicals in Sweden) using HCl-Tris buffer (5 mM, pH 7.4) (the size of the column: radius 3 cm, height 15 cm). The efficiency of hemoglobin capsulized in the endoplasmic reticulum was 29%, the weight ratio of hemoglobin to lipid was 1.5 mg/mg, the average particle size was 309.3±71.5 nm and the methemoglobin content was 3.0%.

Said hemoglobin endoplasmic reticulum solution 4 ml was charged in a 5 ml brown vial and the vial was sealed with a rubber stopper. Argon gas was blown into the solution for 20 minutes and carbon monoxide for 3 minutes at room temperature.

The gamma ray polymerization of said endoplasmic reticulum in the vial was carried out in an ice Dewar vessel. The amount of irradiation of gamma ray was 0.73 Mrad. The progress of the polymerization reaction was confirmed by determining the decrease of absorbance (244–255 nm) due to the diene radicals in the ultraviolet absorption spectrum. The yield of polymerization was 85%.

The solution containing the polymerized endoplasmic reticulum was cooled in an ice-water bath while 60 W white light was exposed for one hour with bubbling an oxygen gas through the solution to convert to a corresponding oxygen complex (oxyhemoglobin; $\lambda_{max}$:415, 541 and 576 nm). The removal of carbon monoxide was confirmed by determining a visible absorption spectrum. The average particle size after the polymerization was 294.3±59.3 nm which was almost the same value of that before the polymerization.

The dependence of oxygen partial pressure on hemoglobin was measured by a visible absorption spectrum and the oxygen dissociation curve was determined with a hemox analyzer (TCS Medical Product Company in U.S.A.) in a 5 mM Tris buffer (pH 7.4) at 37° C. according to a conventional method. As a result, the oxygen affinity ($P_{50}$: oxygen partial pressure required to oxygenate hemoglobin of 50%) of hemoglobin enclosed in the polymerized endoplasmic reticulum was 40 mmHg, the Hill coefficient was 1.65 and the efficiency carrying oxygen between the lungs and peripheral tissues was 38%. Further, it was found that said deoxyhemoglobin was rapidly bonded to oxygen (the oxygen rebinding was finished in 10 msec.) in a 5 mM Tris buffer (pH 7.4) at 37° C. and an oxygen partial pressure of 149 mmHg by laser flash photolysis measurement (with a USP-500 type apparatus manufactured by Unisoku Company in Japan) according to a conventional method.

It is concluded that the hemoglobin which is enclosed in the polymerized endoplasmic reticula synthesized in these examples has oxygen carrying ability equal to that of hemoglobin in red blood cells.

REFERENCE EXAMPLE 1

The effect of the kinds of fatty acids on the hemoglobin containing efficiency was studied according to Example 5 (then, nonpolymerized endoplasmic reticulum before the polymerization reaction was prepared and analyzed).

The results are shown in the following table. Comparing the polymerizable fatty acid (octadecadiene acid) used as a negative charge component with other nonpolymerizable fatty acids, it was found that the former gives higher hemoglobin containing efficiency and higher ratio of hemoglobin (Hb) / lipid than those of the latter.

TABLE

| Fatty acid | Carbon Number | Ene Number | Hb containing efficiency | Hb/lipid |
|---|---|---|---|---|
| Myristic acid | 14 | 0 | 14 | 1.6 |
| Palmitic acid | 16 | 0 | 21 | 1.7 |
| Stearic acid | 18 | 0 | 20 | 1.4· |
| Oleic acid | 18 | 1(cis) | 23 | 1.5 |
| Linoreic acid | 18 | 2(cis) | 17 | 1.8 |
| Octadecadienoic acid (ODA) | 18 | 2(trans) | 20 | 1.9 |

Mole ratio of polymerizable phospholipid/cholesterol/fatty acid = 7/7/2, hemoglobin concentration = 17 wt % and lipid concentration = 5 wt %.

Furthermore, when the fatty acid was not used, the hemoglobin containing efficiency was low (less than 10%). Accordingly, the addition of a fatty acid as a membrane component is apparently efficient.

REFERENCE EXAMPLE 2

A solution of polymerized an endoplasmic reticulum enclosing hemoglobin, which was obtained by the same method as in Example 7, was concentrated by ultrafiltration (an ultrafiltration membrane removable compounds having a molecular weight of 20,000 or less was used) to obtain a concentrated solution having a hemoglobin concentration of 10 g/dl. The physical properties of the solution obtained were measured. The results are shown in the following table. The properties of the solution of the hemoglobin endoplasmic reticulum obtained by the examples of the present invention are apparently equal to those of human blood.

| pH | Results of measurement of the properties | | |
|---|---|---|---|
| | Rotational viscosity (mPa · s, 37.° C.)[1] | Osmotic pressure (mOsm) | Colloidal osmotic pressure (mmHg)[2] |
| 7.4 | 8.4 (7.5) | 320 | 1.0 (35) |
| | 7.5 (18.75) | | |
| | 6.8 (37.5) | | |
| | 6.1 (75) | | |
| | 5.6 (150) | | |

[1] Parenthesized values are share rates ($s^{-1}$).
[2] Parenthesized values are corrected by adding dextran (molecular weight 3.9 × $10^4$) of 3 wt % to the endoplasmic reticulum solution.

REFERENCE EXAMPLE 3

The stability of the polymerized endoplasmic reticulum enclosing hemoglobin which was obtained in Example 7 was studied.

After storing the solution at 4° C. in a dark place for 3 months, the average size of the particles was not changed. Further, no leak of hemoglobin was found (the amount of leak was determined with a gel permeation chromatograph on Sepharose CL-4B.).

After freezing at −80° C., the solution was thawed at room temperature, no leak of hemoglobin from the endoplasmic reticulum was found. No change of the particle size was found. The other hand, in case of the nonpolymerized endoplasmic reticulum, about 30% of the enclosed hemoglobin was leaked. When a surface active agent (Triton X-100) of 20 wt % was added to the endoplasmic reticulum, the polymerized endoplasmic reticulum was stable, and there is no leak of hemoglobin from the endoplasmic reticulum.

As a result, it is found that the polymerized endoplasmic reticulum was synthesized by the same method as in Example 7 was physically stable and possible to maintain for a log time.

REFERENCE EXAMPLE 4

As a method for determining the surface charge of the polymerized endoplasmic reticulum enclosing hemoglobin which was obtained in Example 7, Zeta potential was determined (equipment:Laser Zee model 501 manufactured by Pen Kem Company). The potential of said endoplasmic reticulum was −17.1mv and was almost equal to that of red brood cell.

We claim:

1. A macromolecular endoplasmic reticulum which comprises a polymer obtained by polymerization of a mixture containing one or more polymerizable 2,4-diene phospholipids, cholesterol and one or more polymerizable 2,4-diene fatty acids, wherein the polymerizable 2,4-dienes are concentrated at the polar end of the fatty acids or the fatty acid component of the phospholipid.

2. a macromolecular endoplasmic reticulum which comprises a polymer obtained by polymerization of a mixture containing one or more polymerizable 2,4-diene phospholipids, cholesterol and one or more polymerizable 2,4-diene fatty acids, wherein the polymerizable 2,4-diene phospholipid is a compound represented by the following formula (I) or (II) and at least one of the polymerizable 2,4-diene fatty acids is a compound represented by the following formula (III):

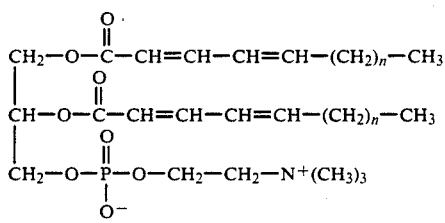 (I)

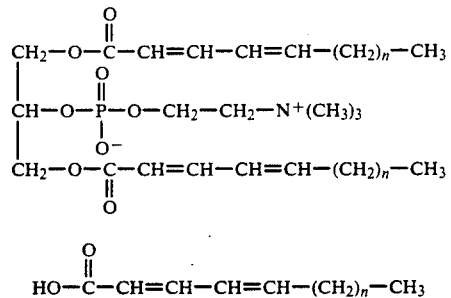

wherein n is an integer 6, 8, 10 or 12.

3. The macromolecular endoplasmic reticulum according to claim 1 or 2, wherein a hemoglobin aqueous solution is capsulated in the endoplasmic reticulum.

4. The macromolecular endoplasmic reticulum according to claim 1 or 2, wherein the mole ratio of the polymerizable phospholipid and cholesterol is 1:2 to 3:2.

5. The macromolecular endoplasmic reticulum according to claim 3, wherein the mole ratio of the polymerizable phospholipid and cholesterol is 1:2 to 3:2.

6. The macromolecular endoplasmic reticulum according to claim 1 or 2, wherein the mole ratio of the polymerizable phospholipid and the polymerizable fatty acid is 5:1 to 3:1.

7. The macromolecular endoplasmic reticulum according to claim 3, wherein the mole ratio of the polymerizable phospholipid and the polymerizable fatty acid is 5:1 to 3:1.

8. The macromolecular endoplasmic reticulum according to claim 4, wherein the mole ratio of the polymerizable phospholipid and the polymerizable fatty acid is 5:1 to 3:1.

* * * * *